United States Patent [19]
Reddy et al.

[11] Patent Number: 5,770,723
[45] Date of Patent: Jun. 23, 1998

[54] PROCESSES FOR PURIFYING SYNTHETIC OLIGONUCLEOTIDES

[76] Inventors: M. Paraweswara Reddy, 219 Valverde Ave.; Firdous Farooqui, 1520 Alexander Ct., both of Brea, Calif. 92821

[21] Appl. No.: 815,787

[22] Filed: Mar. 12, 1997

[51] Int. Cl.$^6$ ...................................................... C07H 21/00
[52] U.S. Cl. ........................................ 536/25.4; 536/25.41
[58] Field of Search ................................. 536/25.4, 25.41

[56] References Cited

FOREIGN PATENT DOCUMENTS 88-300451  1/1988  European Pat. Off. .

OTHER PUBLICATIONS

"Fast Cleavage and Deprotection of Oligonucleotides", M.P. Reddy et al., Tetrahedron Letters, vol. 35, No. 25, pp. 4311–4314, 1994 (Elsevier Science Ltd., Printed in Great Britain).

"A New, Reliable Cartridge for the Rapid Purification of Synthetic DNA", L.J. McBride et al., 362 BioTechniques, vol. 6, No. 4 (1988).

*Primary Examiner*—Scott W. Houtteman
*Attorney, Agent, or Firm*—William H. May; P. R. Harder

[57] ABSTRACT

Purification of synthesized oligonucleotides is achieved using novel processes and reagents. The novel processes involve adding certain salts to treated synthesized oligonucleotides prior to eluting the oligonucleotides from reverse phase purification cartridges. The novel processes also involve treating synthesized oligonucleotides using cleaving and deprotecting reagents containing methylamine and certain salts. Reagents comprising methylamine and certain salts can be used to rapidly cleave and deprotect oligonucleotides while obtaining high yields of purified oligonucleotides using reverse phase purification technologies.

58 Claims, 4 Drawing Sheets

PROCESSES FOR PURIFYING SYNTHETIC OLIGONUCLEOTIDES

BACKGROUND OF THE INVENTION

1. Field of the Invention

The present invention relates to processes and reagents for synthesizing and purifying oligonucleotides. More particularly, the present invention involves reagents and methods for purifying synthetic oligonucleotides using reverse phase purification technologies.

2. Description of Relevant Art

During the last decade the availability of oligonucleotides has become increasingly important to molecular biologists and cell biologists. In order to meet the growing demand for oligonucleotides synthetic oligonucleotide technology has emerged. This technology includes new nucleotide derivatives capable of reacting in a building block manner to form synthetic oligonucleotides and reagents associated with their synthesis.

One common synthetic method involves sequentially adding nucleotide derivatives to a growing oligonucleotide chain attached at one terminus to a solid support. Once the desired oligonucleotide sequence is made, the synthetic procedure typically involves deprotecting previously protected active amino and cleaving the oligonucleotide from the solid support. Until recently the most common deprotecting and cleaving reagent was ammonium hydroxide. While providing good yields with little side reactions, the kinetics of the ammonium hydroxide cleaving and deprotecting reactions are very slow and require on the order of four hours to deprotect and cleave newly synthesized oligonucleotides. In order to overcome this undesirably slow post synthetic processing step, new deprotecting and cleaving reagents have been developed. In particular, methylamine containing reagents have reduced dramatically the deprotection and cleavage reaction time.

One drawback associated with methylamine containing cleaving and deprotection reagents is the apparent reduction in yield of oligonucleotides purified using reverse phase techniques. In a typical reverse phase purification process, purification of oligonucleotides involves loading the oligonucleotide on a reverse phase cartridge and eluting purified oligonucleotide. Functional groups, usually lipophilic trityl groups, on the oligonucleotides interact hydrophobically with the reverse phase cartridge. The efficiency of reverse phase cartridge purification depends in part on the strength of this hydrophobic interaction. When methylamine containing deprotection and cleaving reagents are used, methylamine in the synthesized oligonucleotide solution as it passes through the reverse phase purification cartridge interferes with the hydrophobic interaction of the oligonucleotide with the reverse phase purification cartridge to a greater degree than when the more hydrophilic ammonium hydroxide is the sole component of the deprotection and cleaving reagent. The decreased hydrophobic interaction of the oligonucleotide with the reverse phase cartridge results in low recoveries of the synthesized oligonucleotides in the cartridge eluents.

Accordingly, there is a need to provide processes for producing purified synthetic oligonucleotides with high yields using reverse phase purification technologies. There is also a need for oligonucleotide deprotection and cleaving reagents having fast deprotection and cleaving kinetics which additionally allow for high yields of purified oligonucleotides when used in connection with reverse phase purification techniques.

SUMMARY OF THE INVENTION

The present invention accomplishes the above identified needs by providing processes and reagents which when used in oligonucleotide synthesis procedures contribute to the fast production and high yield of purified oligonucleotides. The processes and reagents of the present invention are based upon the discovery that when fast deprotection and cleavage reagents containing methylamine are used in combination with reverse phase oligonucleotide purification techniques, the presence of certain salts significantly enhances the yield of purified oligonucleotides.

More particularly, the present invention provides processes which include adding sodium chloride and/or ammonium acetate to a synthesized oligonucleotide treated with a cleaving and deprotection reagent containing methylamine. The sodium chloride and/or ammonium acetate is added to the oligonucleotide solution prior to purification of the oligonucleotide using reverse phase technologies. Preferably the synthesized oligonucleotide is attached at one terminus to a solid support and has protected exocyclic amino functionalities so that the treating step results in deprotecting the protected amino functionalities and cleaving the synthetic oligonucleotide from the solid support. The addition of sodium chloride and/or ammonium acetate prior to the purification step significantly enhances the recovery of purified synthetic oligonucleotide from a reverse phase purification cartridge.

The additional step of adding sodium chloride and/or ammonium acetate to the treated oligonucleotide is avoided and a single reagent can be used for both treating and purifying synthetic oligonucleotide with a preferred embodiment of the present invention in which synthesized oligonucleotide is treated with a cleaving and deprotecting reagent containing methylamine and sodium chloride and/or ammonium acetate. The presence of sodium chloride in the treating step, however, has the effect of slowing the deprotection and cleaving kinetics. Accordingly, a most preferred embodiment is a process for producing purified synthesized oligonucleotide including treating synthesized oligonucleotides with a composition of methylamine and ammonium acetate, loading the deprotected and cleaved oligonucleotide on a reverse phase purification cartridge, eluting the oligonucleotide from the reverse phase cartridge and recovering purified synthetic oligonucleotide from the reverse phase purification cartridge eluate.

Deprotecting and cleaving reagents of the present invention include compositions of methylamine and an additive of ammonium acetate and/or sodium chloride. The methylamine is preferably a solution of about 40 wt % methylamine in water and the additive is preferably about 0.5M in water. In preferred embodiments the deprotecting and cleaving reagent composition is about 40 wt % aqueous methylamine and about 0.5M ammonium acetate at a volume ratio of from about 1:1, respectively, to about 1:9, respectively. A more preferred embodiment of the deprotecting and cleaving reagent is about 40 wt % methylamine and about 0.5M ammonium acetate at a volume ratio of from about 1:1 to about 1:3, respectively. A most preferred embodiment is a reagent having about 40 wt % methylamine and about 0.5M ammonium hydroxide at a volume ratio of about 1:3, respectively.

Advantageously, the processes and reagents of the present invention can be used in combination with well known synthetic methods to provide deprotected, cleaved, and purified synthetic oligonucleotide in high yield.

The foregoing and additional features and advantages of this invention will become apparent from the detailed description and accompanying drawings that follow.

DETAILED DESCRIPTION OF THE INVENTION

Figure 1A:
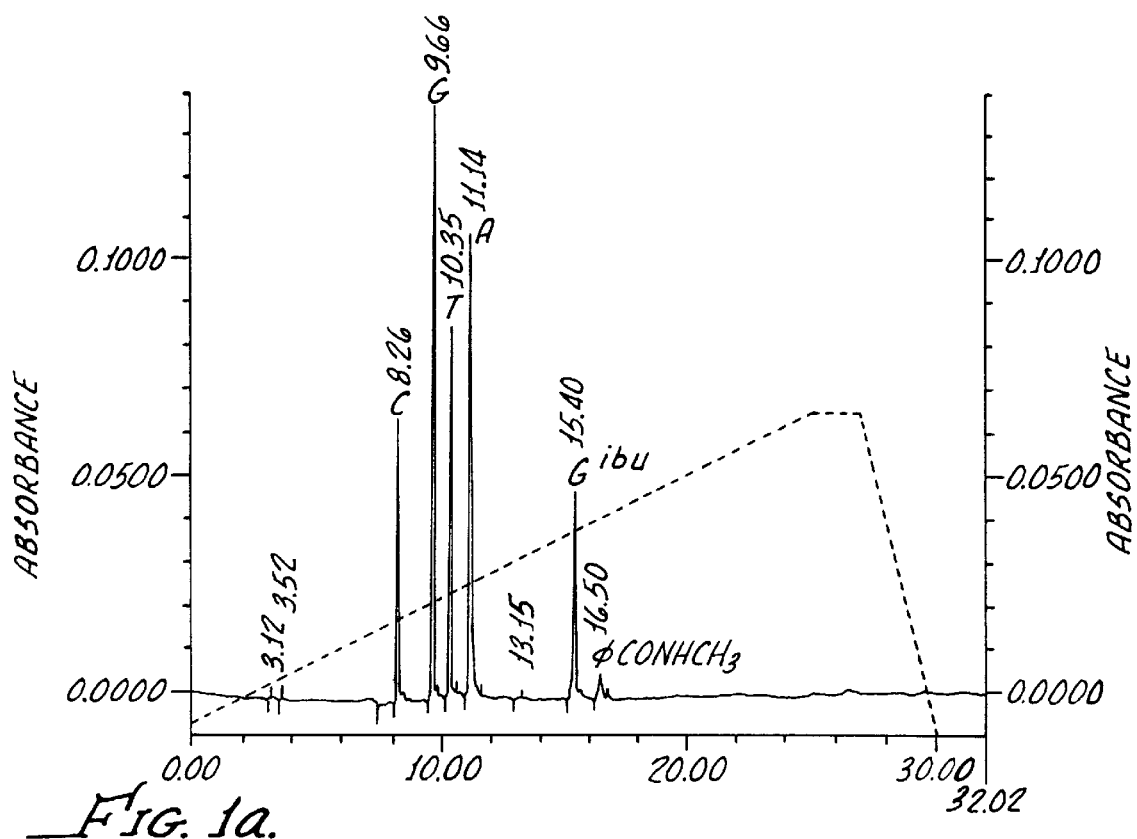
FIG. 1(a)–(b) depicts HPLC scans showing the deprotection kinetics of a 21 mer oligonucleotide treated in accordance with embodiments of the present invention.

The present invention provides processes and reagents useful in the synthesis of oligonucleotides. When used in connection with cleaving and/or deprotecting synthesized oligonucleotides in combination with reverse phase purification techniques, the present invention provides fast deprotecting and cleaving kinetics and high yield purified synthetic purified oligonucleotides. Most typically, the present invention is carried out during oligonucleotide synthesis procedures which involve synthesizing oligonucleotide by standard known synthetic methods including, but not limited to, the well known phosphoramidite synthetic procedures. As known in the art, in such processes, subsequent to adding the final nucleotide during the successive addition of nucleotides to a growing oligonucleotide chain, deprotecting the protected exocyclic amines on the oligonucleotides is carried out. In processes in which the synthesis is carried out with the growing oligonucleotide chain attached to a solid support, the deprotecting step is performed with the same reagent and simultaneous with a cleaving step in which the completed oligonucleotide is cleaved from the solid support. Following the deprotection and cleaving procedures, these processes are typically followed by a purification step. In most processes, the purification step involves eluting the synthesized, deprotected and cleaved oligonucleotide in the deprotection and cleaving reagent through a reverse phase purification cartridge.

The present invention provides improved processes and reagents for deprotecting, cleaving and purifying synthesized oligonucleotides. Advantageously, embodiments of the present invention provide deprotected and cleaved oligonucleotides in very fast deprotection and cleaving reactions. As an added feature, the reagents of the present invention provide purified oligonucleotide in high yield.

More particularly, and in one aspect, the present invention involves adding a composition comprising an additive to a treated synthetic oligonucleotide prior to purification using reverse phase techniques. The oligonucleotide preferably has been treated with a methylamine containing deprotecting and cleaving reagent having very fast deprotection and cleaving kinetics. The additive can be ammonium acetate and/or sodium chloride and the synthetic oligonucleotide preferably has exocyclic amino groups, which, as known in the art, are protected with an amino protecting group. Preferably, the oligonucleotide is attached at the 3' or 5' terminus to a solid support. In oligonucleotide synthesis procedures which further include a purification step, such a step is carried out by loading the cleaved and deprotected oligonucleotide in the aqueous solution of methylamine and additive on to a purification column. Preferably the purification column is a reverse phase cartridge. Those skilled in the art are credited with the knowledge of the variety of such reverse phase cartridges and their use. Suitable cartridges include the $C_8$–$C_{18}$ cartridge available from Applied Biosystems, Foster City, Calif.; Glen Research, Sterling, Va. or Clontech Laboratories Inc., Palo Alto, Calif. After loading the cleaved and deprotected oligonucleotide on to the chromatographic cartridge, eluting the oligonucleotide from the column is accomplished using an aqueous organic solvent system such as a combination of acetonitrile and water. After the cleaved and deprotected oligonucleotide solution elutes from the column, recovery of purified oligonucleotide is accomplished by simply evaporating off the solvent, to dryness. The recovery of the resulting purified oligonucleotide is improved over conventional purified procedures.

Preferably, when the protected oligonucleotide contains protected functionalities in addition to the protected exocyclic amino groups, e.g. protected hydroxyl groups, the present invention further includes deprotecting the protected hydroxy functionality after loading the cleaved and deprotected oligonucleotide on the reverse phase cartridge and prior to eluting the oligonucleotide from the reverse phase cartridge. For example, when the 5' OH is protected with DMT, or other group as known in the art, the OH is freed by deprotecting the acid labile group with a suitable acid. When DMT is the protecting group, detritylation occurs on the reverse phase cartridge, prior to elution, by detritylation with an aqueous trifluoroacetic acid solution.

In preferred embodiments of the present invention, the methylamine containing composition for treating the synthesized oligonucleotide further contains ammonium hydroxide. Ammonium hydroxide is available in a 29 wt % aqueous solution from Aldrich Chemical Company. When ammonium hydroxide is present in the composition for treating the oligonucleotide, a volume ratio of 1:1 ammonium hydroxide to 40 wt % aqueous methylamine (also available from Aldrich Chemical Company, Milwaukee, Wis.) is preferred. This ammonium hydroxide and methylamine composition, called AMA, provides fast cleaving and deprotection of synthesized oligonucleotides. According to the invention, adding certain salts prior to purification using a reverse phase cartridge results in high yields of purified synthetic oligonucleotide.

The added salts can be solid or aqueous solutions of sodium chloride and/or ammonium acetate. In certain embodiments 0.5M solutions of sodium chloride and/or ammonium acetate are combined with the treated oligonucleotide solution such that the volume ratio of methylamine or AMA in the treated oligonucleotide solution and the added aqueous salt solution is from about 1:1 to about 1:9, respectively. Preferably, the ratio of methylamine or AMA to sodium chloride or ammonium acetate is from about 1:1 to about 1:3, respectively. Most preferably, the ratio is about 1:3 methylamine or AMA to sodium chloride or ammonium acetate.

In another aspect of the invention, it is advantageous to use a single reagent for treating and purifying synthesized oligonucleotides. In this way, the step of adding salts to the treated synthesized oligonucleotide prior to purification in a reverse phase cartridge is eliminated. In this embodiment of the invention, the synthesized oligonucleotide is treated with a composition of methylamine or AMA containing sodium chloride or ammonium acetate.

It was discovered, however, that adding sodium chloride to the composition for treating the synthesized oligonucleotide slowed the deprotection kinetics of the treating step. Accordingly, a preferred embodiment of this aspect of the invention is to treat synthesized oligonucleotides with a composition comprising methylamine or AMA and an additive comprising ammonium acetate.

In this preferred embodiment of the invention, the deprotection and cleaving reaction is fast, requiring as little as about 5 minutes at 65° C. and typically is carried out by contacting a solid support containing the protected and attached oligonucleotide with an aqueous solution of about 40 wt % methylamine (or about 1:1 40 wt % methylamine to 29 wt % ammonium hydroxide) and an additive comprising ammonium acetate. Following treatment with methylamine or AMA and ammonium acetate solution, the exocyclic amino groups become deprotected and the oligonucleotide is cleaved from the solid support.

As described above, reagents of the present invention include compositions of aqueous methylamine and at least one additive selected from ammonium acetate and sodium chloride. In preferred embodiments, the solution contains from about 1:1 to about 1:3 volume ratio of about 40 wt % methylamine in water to about 0.5M ammonium acetate or 0.5M sodium chloride. In addition to methylamine, reagents of the present invention can contain ammonium hydroxide cleaving and deprotection reagent. Embodiments of the present invention containing ammonium hydroxide typically are solutions containing from about 1:1 to 1:9 volume ratio of about 1:1 methylamine to ammonium hydroxide to about 0.5M ammonium acetate or 0.5M sodium chloride. Preferred embodiments contain volume ratios of from about 1:1 to 1:3 methylamine or AMA to ammonium acetate or sodium chloride, with 1:3 being the most preferred ratio. It will be appreciated that the concentrations of the component solutions used in any of the above embodiments can be varied so long as the relative amounts of the components in the resulting reagent solution is the same.

Although not in anyway limiting the present invention, the following examples provide a more thorough description and understanding of the reagents and methods described herein.

EXAMPLE 1

Synthesis of Oligonucleotides

Oligonucleotides were synthesized on an ABI 394 DNA synthesizer by solid phase methodology (Oligonucleotide Synthesis, a practical approach, edited by M. J. Gait, IRL press, 1984). The synthesis was performed on a 0.2 umole scale using CPG solid supports containing 3'-nucleoside. 5'-DMT $A^{bz}$, $C^{ac}$, $G^{ibu}$ and T phosphoramidites were used and they were activated with tetrazole during the coupling reaction. Aqueous iodine was used for oxidation and acetic anhydride with N-methylimidazole was used for capping the unreacted 5'-hydroxyl groups. The DMT group was left on the oligonucleotide after the completion of the solid support synthesis for purification purposes. Finally, when the desired length of oligonucleotide was obtained, it was cleaved and deprotected as described in Example 2.

The following sequences were synthesized:
15 mer: 5' CGC.CAG.GGT.TTT.CCT$^{3'}$
21 mer: 5' CTG.GTC.AGT.TGT.CAT.ACT.GCT$^{3'}$
35 mer: 5' GAT.GCC.AGT.TCG.GTC.ATA.CAC.GTA.GTA.CTA.CGA.CT$^{3'}$

EXAMPLE 2

Cleavage and Deprotection of Oligonucleotides

The oligonucleotides synthesized on solid supports, as described in Example 1, were cleaved with either concentrated NH$_4$OH (700 ul) for 1 hour at room temperature or AMA (ammonium hydroxide/methylamine, 1:1, 700 ul) or methylamine (700 ul) for 5 minutes at room temperature (M. P. Reddy et al, Tetrahedron Letters, 1994, 35 4311–4314). The cleaved oligonucleotide was taken in a vial, sealed and heated at 65° C. for 3 hours for deprotection with NH$_4$OH or 5 minutes for deprotection with AMA or methylamine.

The cleaved and deprotected oligonucleotide was purified as described in Example 3.

EXAMPLE 3

Purification of Oligonucleotides Using Reverse Phase Cartridges

A reverse phase cartridge (obtained from ABI, Foster City, Calif., Glen Research, Sterling, Va. or Clontech Laboratories Inc., Palo Alto, Calif.) was connected to a 10 ml polypropylene syringe. All fittings were made tight. All solutions were passed through the syringe barrel mounted on the cartridge. The syringe was removed from the cartridge before removing the plunger and the syringe barrel was re-inserted prior to the next addition. The cartridges were immobilized with a laboratory clamp. The following steps were performed:

1. 5 ml of acetonitrile were passed through the cartridge to waste.
2. 5 ml of 2M TEAA (triethylammonium acetate buffer) were passed through the cartridge to waste.
3. The ammonia solution (700 ul) containing oligonucleotide was diluted with an equal volume of water (700 ul) or the AMA (700 ul) or methylamine solution (700 ul) containing oligonucleotide was diluted with 3 times 0.5M NaCl (2.1 ml) or 0.5M ammonium acetate solution (2.1 ml). The diluted solution was passed through the cartridge at a rate of about 1 drop per second and the eluate was collected.
4. The eluate was passed through the cartridge a second time.
5. 5 ml of dilute ammonium hydroxide (1:9 dilution of concentrated ammonium hydroxide in deionized water) were passed through the cartridge to waste, followed by 10 ml of water.
6. The syringe barrel was filled with 5 ml of 3% TFA (trifluoroacetic acid) in water and a portion passed through to waste to effect detritylation. The remaining acid was let stand in the cartridge 5 minutes, then the remainder was flushed through to waste.
7. 10 ml of water were passed through to waste.
8. The purified, detritylated oligonucleotide was eluted and collected by slowly passing, drop-by-drop, 1.5 ml of 20% acetonitrile through the cartridge. The purified oligonucleotide was evaporated to dryness.

The efficiency of the reverse phase cartridge purification is shown by the data in Table 1.

TABLE 1

| Reverse Phase Cartridge Purification of Oligonucleotides | | |
|---|---|---|
| Length | Reagent | % Bound/Released |
| 21 mer | NH$_4$OH + H$_2$O (1:1) | 35.89% |
| 21 mer | AMA + H$_2$O (1:1) | 25.05% |
| 21 mer | AMA + 0.5M NaCl (1:1) | 30.79% |
| 21 mer | AMA + 0.5M NaCl (1:3) | 35.28% |
| 21 mer | AMA + 0.5M NH$_4$OAc (1:1) | 32.14% |
| 21 mer | AMA + 0.5M NH$_4$OAc (1:3) | 39.04% |
| 21 mer | MA + H$_2$O (1:3) | 24% |
| 21 mer | MA + 0.5M NaCl (1:3) | 36.55% |
| 21 mer | MA + 0.5M NH$_4$OAc (1:3) | 38.25% |
| 15 mer | NH$_4$OH + H$_2$O (1:1) | 40.83% |
| 15 mer | AMA + 0.5M NH$_4$OAc (1:3) | 39.22% |
| 35 mer | NH$_4$OH + H$_2$O (1:1) | 26.02% |
| 35 mer | AMA + 0.5M NH$_4$OAc (1:3) | 28.10% |

AMA: Ammonium hydroxide:MethylAmine (1:1)
Ammonium hydroxide is a 29% aqueous solution. Methylamine is a 40% aqueous solution. Both are obtained from Aldrich Chemical Company, Milwaukee, Wis.

EXAMPLE 4

Deprotection Kinetics

The 21 mer oligonucleotides synthesized in Example 1 were cleaved and deprotected with either AMA (1:1) containing 0.5M NaCl (700 ul) or AMA (1:1) containing 0.5M ammonium acetate. They were cleaved for 5 minutes at room temperature and deprotected for 5 minutes at 65° C. The oligonucleotide solutions were evaporated and digested with phosphodiesterase and alkaline phosphatase for 1 hour at room temperature and analyzed by reverse phase HPLC. The conditions for the HPLC were: $C_{18}$ Microsorb column (Rainin) 5u particles, 4.6 mm×25 cm; Bottle A contained: 0.1M ammonium acetate, pH 6.9; Bottle B contained: HPLC grade acetonitrile; the flow rate was 1 ml/minute, 0–20 minutes gradient to 15% B, 20–25 minutes gradient to 25% B, 25–27 minutes gradient to 50% B, 27–30 minutes gradient to 50% B, and 30–35 minutes gradient to 0% B. The HPLC scans are shown in FIG. 1.

Figure 1B:
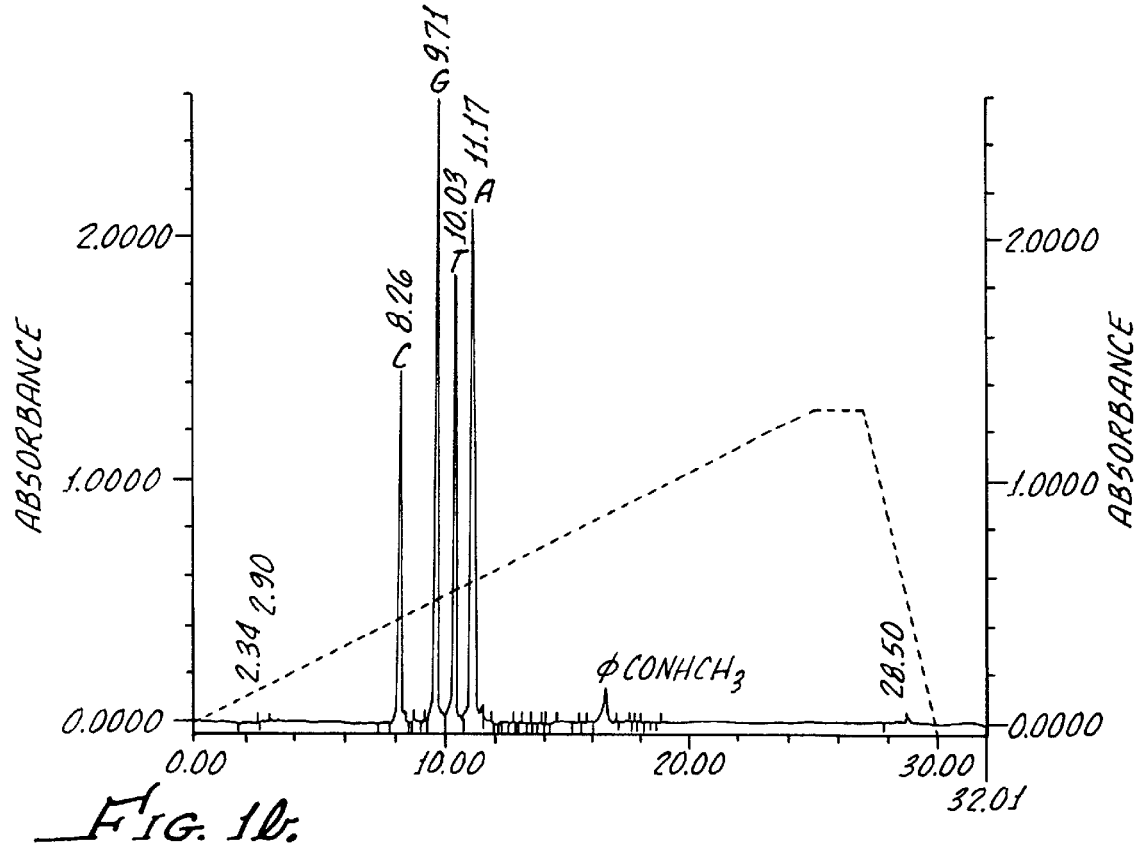

FIG. 1(a) shows the deprotection kinetics of a 21 mer oligonucleotide cleaved and deprotected with a solution of AMA and 0.5M NaCl. Remaining $G^{ibu}$ indicates that the deprotection was slower than desired. FIG. 1(b) shows the deprotection kinetics for a 21 mer oligonucleotide cleaved and deprotected with a solution of AMA and 0.5M ammonium acetate in accordance with a preferred embodiment of the present invention.

EXAMPLE 5

Analysis of Oligonucleotide by Capillary Electrophoresis

The purified oligonucleotides were analyzed by capillary electrophoresis on a P/ACE 5000 instrument available from Beckman Instruments, Inc. The capillary gel column (U100P urea Gel column) was obtained from Beckman Instruments, Inc. and was loaded and cut to 37 cm long. The Tris-borate, 7M urea buffer (also obtained from Beckman Instruments, Inc.) was used according to directions. The absorbances of the oligonucleotides were in the range of 1 to 2 $OD/_{260\ nm}$/ml, depending upon the quality and length of the oligonucleotide. Injection was at 10 kV for 3 seconds, while separation was at 11 kV for 30–45 minutes, depending upon the length of the oligonucleotide. The capillary electrophoresis scans are shown in FIG. 2.

Figure 2A:
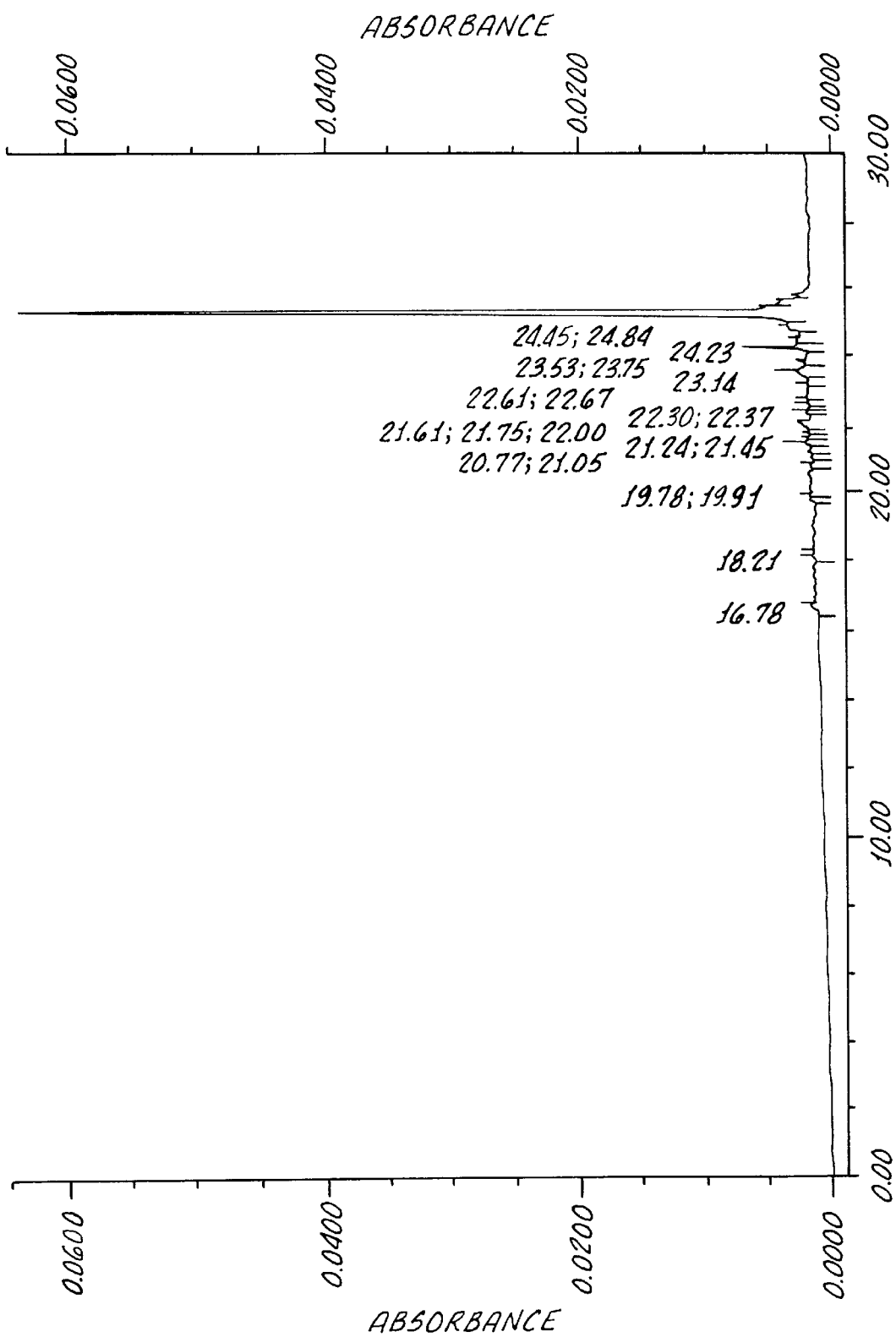
FIG. 2 depicts capillary electrophoresis scans for a 21 mer oligonucleotide purified in accordance with embodiments of the present invention.
Figure 2B:
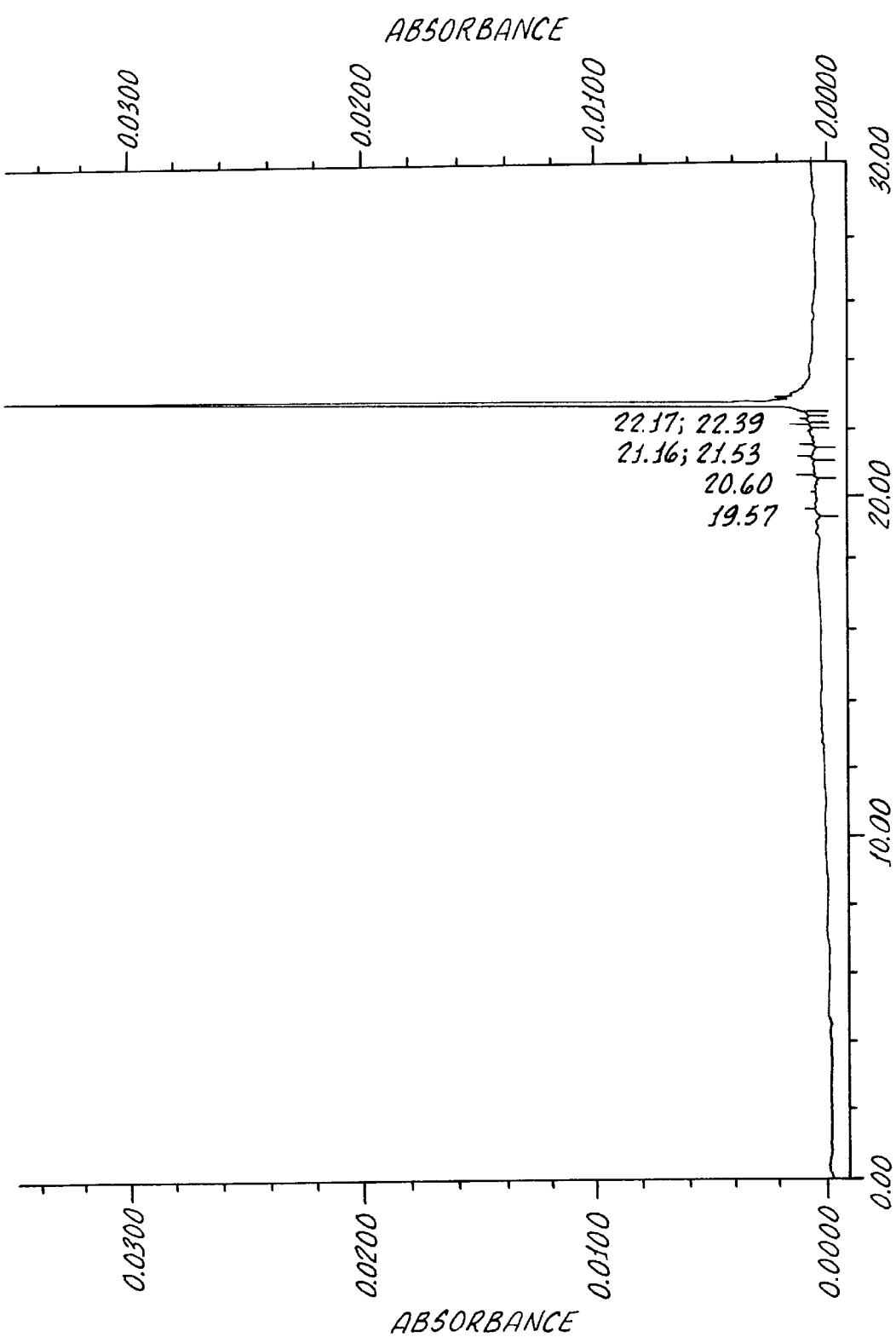
Figure 2C:
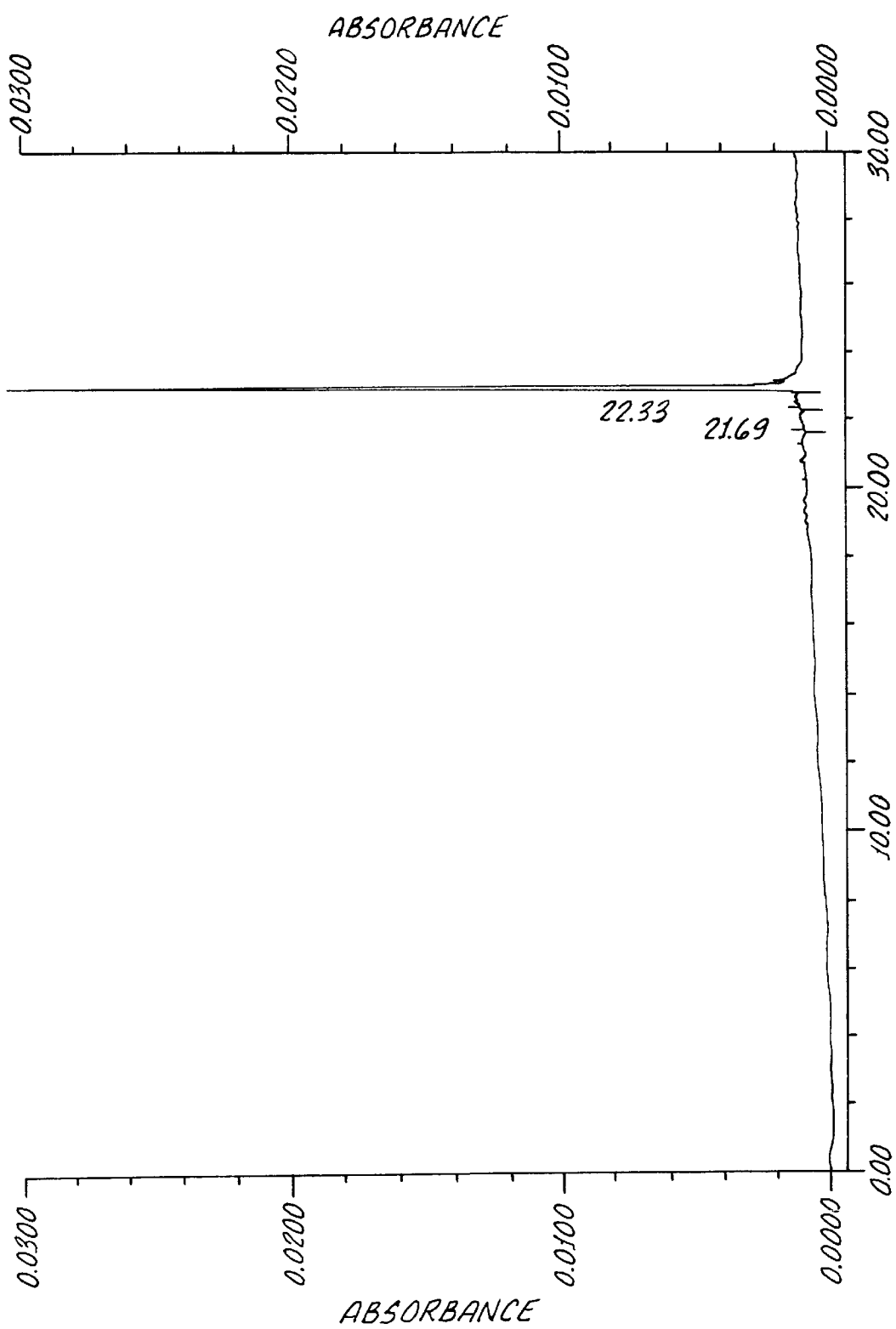

FIG. 2(a) is the capillary electrophoresis scan for the crude 21 mer oligonucleotide. FIG. 2(b) is the scan for the 21 mer oligonucleotide, cleaved and deprotected with a solution of ammonium hydroxide and water (1:1), after reverse phase cartridge purification. FIG. 2(c) is the scan for the 21 mer oligonucleotide, cleaved and deprotected with a solution of AMA and 0.5M ammonium acetate (1:3), after reverse phase cartridge purification. These figures indicate that the AMA and ammonium acetate solution worked as well as ammonium hydroxide in purifying the treated oligonucleotide, however, the cleaving and deprotection time was significantly lower at 10 minutes compared to 4 hours.

Although the present invention has been described with reference to specific examples, those examples are in no way to be construed as limiting the reagents and processes of the present invention. It will be appreciated by persons skilled in the art that the present invention is not limited to what has been shown and described hereinabove, but is to be determined solely in terms of the following claims.

We claim:

1. A process for preparing purified synthesized oligonucleotide, said process comprising the steps of:
   providing synthesized oligonucleotide, said oligonucleotide being attached to a solid support and having protected exocyclic amino functionalities,
   treating said synthesized oligonucleotide with a composition comprising methylamine,
   adding to said treated synthesized oligonucleotide a composition comprising an additive selected from the group consisting of sodium chloride and ammonium acetate,
   loading said treated synthesized oligonucleotide and additive on a reverse phase purification cartridge,
   eluting said treated synthesized oligonucleotide from said reverse phase purification cartridge; and
   recovering purified synthesized oligonucleotide from said reverse phase purification cartridge eluate.

2. The process of claim 1 wherein said synthesized oligonucleotide has protected hydroxy functionalities.

3. The process of claim 2 further including the step of deprotecting the protected hydroxy functionalities prior to eluting said treated synthesized oligonucleotide from said reverse phase purification cartridge.

4. The process of claim 1 wherein said methylamine is about 40 wt % methylamine in water.

5. The process of claim 4 wherein said additive is about 0.5M sodium chloride and said about 40 wt % methylamine and said about 0.5M sodium chloride are present in said treated synthesized oligonucleotide at a volume ratio of from about 1:1 to about 1:9, respectively.

6. The process of claim 5 wherein said about 40 wt % methylamine and said about 0.5M sodium chloride are present in said treated synthesized oligonucleotide at a volume ratio of from about 1:1 to about 1:3, respectively.

7. The process of claim 6 wherein said about 40 wt % methylamine and said about 0.5M sodium chloride are present in said treated synthesized oligonucleotide at a volume ratio of about 1:3, respectively.

8. The process of claim 4 wherein said additive is 0.5M ammonium acetate and said about 40 wt % methylamine and said about 0.5M ammonium acetate are present in said treated synthesized oligonucleotide at a volume ratio of from about 1:1 to about 1:9, respectively.

9. The process of claim 8 wherein said about 40 wt % methylamine and said about 0.5M ammonium acetate are present in said treated synthesized oligonucleotide at a volume ratio of from about 1:1 to 1:3, respectively.

10. The process of claim 9 wherein said about 40 wt % methylamine and said about 0.5M ammonium acetate are present in said treated synthesized oligonucleotide at a volume ratio of about 1:3, respectively.

11. The process of claim 1 wherein said composition for treating said synthesized oligonucleotide further includes ammonium hydroxide.

12. The process of claim 11 wherein said ammonium hydroxide is about 29 wt % ammonium hydroxide in water.

13. The process of claim 12 wherein said methylamine is about 40 wt % methylamine in water and said about 29 wt % ammonium hydroxide and said about 40 wt % methylamine are present in a volume ratio of about 1:1.

14. The process of claim 13 wherein said additive is about 0.5M sodium chloride and said about 1:1 ratio of about 29 wt % ammonium hydroxide to about 40 wt % methylamine and said about 0.5M sodium chloride are present in said treated synthesized oligonucleotide at a volume ratio of from about 1:1 to about 1:9, respectively.

15. The process of claim 14 wherein said about 1:1 ratio of about 29 wt % ammonium hydroxide to about 40 wt % methylamine and said about 0.5M sodium chloride are present in said treated synthesized oligonucleotide at a volume ratio of from about 1:1 to about 1:3, respectively.

16. The process of claim 15 wherein said about 1:1 ratio of about 29 wt % ammonium hydroxide to about 40 wt % methylamine and said about 0.5M sodium chloride are present in said treated synthesized oligonucleotide at a volume ratio of about 1:3, respectively.

17. The process of claim 13 wherein said additive is 0.5M ammonium acetate and said about 1:1 ratio of about 29 wt % ammonium hydroxide to about 40 wt % methylamine and said about 0.5M ammonium acetate are present in said treated synthesized oligonucleotide at a volume ratio of from about 1:1 to about 1:9, respectively.

18. The process of claim 17 wherein said about 1:1 ratio of about 29 wt % ammonium hydroxide to about 40 wt % methylamine and said about 0.5M ammonium acetate are present in said treated synthesized oligonucleotide at a volume ratio of from about 1:1 to 1:3, respectively.

19. The process of claim 18 wherein said about 1:1 ratio of about 29 wt % ammonium hydroxide to about 40 wt % methylamine and said about 0.5M ammonium acetate are present in said treated synthesized oligonucleotide at a volume ratio of about 1:3, respectively.

20. A process for preparing purified synthesized oligonucleotide, said process comprising the steps of:
providing synthesized oligonucleotide, said oligonucleotide being attached to a solid support and having protected exocyclic amino functionalities,
treating said synthesized oligonucleotide with a composition comprising methylamine and an additive selected from the group consisting of sodium chloride and ammonium acetate,
loading said treated synthesized oligonucleotide on a reverse phase purification cartridge,
eluting said treated synthesized oligonucleotide from said reverse phase purification cartridge; and
recovering purified synthesized oligonucleotide from said reverse phase purification cartridge eluate.

21. The process of claim 20 wherein said synthesized oligonucleotide has protected hydroxy functionalities.

22. The process of claim 21 further including the step of deprotecting the protected hydroxy functionalities prior to eluting said treated synthesized oligonucleotide from said reverse phase purification cartridge.

23. The process of claim 20 wherein said methylamine is about 40 wt % methylamine in water.

24. The process of claim 23 wherein said additive is about 0.5M ammonium acetate and said about 40 wt % methylamine and said about 0.5M ammonium acetate are present in said composition at a volume ratio of from about 1:1 to about 1:9, respectively.

25. The process of claim 24 wherein said about 40 wt % methylamine and said about 0.5M ammonium acetate are present in said composition at a volume ratio of from about 1:1 to about 1:3, respectively.

26. The process of claim 25 wherein said about 40 wt % methylamine and said about 0.5M ammonium acetate are present in said composition at a volume ratio of about 1:3, respectively.

27. The process of claim 20 wherein said composition further includes ammonium hydroxide.

28. The process of claim 27 wherein said ammonium hydroxide is about 29 wt % ammonium hydroxide in water.

29. The process of claim 28 wherein said methylamine is about 40 wt % methylamine in water and said about 29 wt % ammonium hydroxide and said about 40 wt % methylamine are present in a volume ratio of about 1:1.

30. The process of claim 29 wherein said additive is about 0.5M ammonium acetate and said about 1:1 ratio of about 29 wt % ammonium hydroxide to about 40 wt % methylamine and said about 0.5M ammonium acetate are present in said composition at a volume ratio of from about 1:1 to about 1:9, respectively.

31. The process of claim 30 wherein said about 1:1 ratio of about 29 wt % ammonium hydroxide to about 40 wt % methylamine and said about 0.5M ammonium acetate are present in said composition at a volume ratio of from about 1:1 to about 1:3, respectively.

32. The process of claim 31 wherein said about 1:1 ratio of about 29 wt % ammonium hydroxide to about 40 wt % methylamine and said about 0.5M ammonium acetate are present in said composition at a volume ratio of about 1:3, respectively.

33. A process for deprotecting and cleaving oligonucleotides, said process comprising treating synthesized oligonucleotide with a composition comprising methylamine and an additive selected from the group consisting of ammonium acetate and sodium chloride.

34. The process of claim 33 wherein said synthesized oligonucleotide is attached to a solid support and said treating step causes said synthesized oligonucleotide to cleave from said solid support.

35. The process of claim 33 wherein said synthesized oligonucleotide contains protected exocyclic amino functionalities and said treating step results in the deprotection of said protected exocyclic amino functionalities.

36. The process of claim 33 wherein said methylamine is about 40 wt % methylamine in water.

37. The process of claim 36 wherein said additive is about 0.5M ammonium acetate and said about 40 wt % methylamine and said about 0.5M ammonium acetate are present in said composition at a volume ratio of from about 1:1 to 1:9, respectively.

38. The process of claim 37 wherein said about 40 wt % methylamine and said about 0.5M ammonium acetate are present in said composition at a volume ratio of from about 1:1 to 1:3, respectively.

39. The process of claim 38 wherein said about 40 wt % methylamine and said about 0.5M ammonium acetate are present in said composition at a volume ratio of about 1:3, respectively.

40. The process of claim 33 wherein said composition further includes ammonium hydroxide.

41. The process of claim 40 wherein said ammonium hydroxide is about 29 wt % ammonium hydroxide in water.

42. The process of claim 41 wherein said methylamine is about 40 wt % methylamine in water and said about 29 wt % ammonium hydroxide and said about 40 wt % methylamine are present in a volume ratio of about 1:1.

43. The process of claim 42 wherein said additive is about 0.5M ammonium acetate and said about 1:1 ratio of about 29 wt % ammonium hydroxide to about 40 wt % methylamine and said about 0.5M ammonium acetate are present in said composition at a volume ratio of from about 1:1 to about 1:9, respectively.

44. The process of claim 43 wherein said about 1:1 ratio of about 29 wt % ammonium hydroxide to about 40 wt % methylamine and said about 0.5M ammonium acetate are present in said composition at a volume ratio of from about 1:1 to about 1:3, respectively.

45. The process of claim 44 wherein said about 1:1 ratio of about 29 wt % ammonium hydroxide to about 40 wt % methylamine and said about 0.5M ammonium acetate are present in said composition at a volume ratio of about 1:3, respectively.

46. A reagent for cleaving and deprotecting oligonucleotides comprising methylamine and an additive selected from the group consisting of ammonium acetate and sodium chloride.

47. The reagent of claim 46 wherein said methylamine is about 40 wt % methylamine in water.

48. The reagent of claim 47 wherein said additive is about 0.5M ammonium acetate and said about 40 wt % methylamine and said about 0.5M ammonium acetate are present in said reagent at a volume ratio of from about 1:1 to about 1:9, respectively.

49. The reagent of claim 48 wherein said about 40 wt % methylamine and said about 0.5M ammonium acetate are present in said reagent at a volume ratio of from about 1:1 to about 1:3, respectively.

50. The reagent of claim 49 wherein said about 40 wt % methylamine and said about 0.5M ammonium acetate are present in said reagent at a volume ratio of about 1:3, respectively.

51. The reagent of claim 46 further including ammonium hydroxide.

52. The reagent of claim 51 wherein said ammonium hydroxide is about 29 wt % ammonium hydroxide in water.

53. The reagent of claim 52 wherein said methylamine is about 40 wt % methylamine in water and said about 29 wt % ammonium hydroxide and said about 40 wt % methylamine are present in a volume ratio of about 1:1.

54. The reagent of claim 53 wherein said additive is about 0.5M ammonium acetate and said about 1:1 ratio of about 29 wt % ammonium hydroxide to about 40 wt % methylamine and said about 0.5M ammonium acetate are present in said reagent at a volume ratio of from about 1:1 to about 1:9, respectively.

55. The reagent of claim 54 wherein said about 1:1 ratio of about 29 wt % ammonium hydroxide to about 40 wt % methylamine and said about 0.5M ammonium acetate are present in said reagent at a volume ratio of from about 1:1 to about 1:3, respectively.

56. The reagent of claim 55 wherein said about 1:1 ratio of about 29 wt % ammonium hydroxide to about 40 wt % methylamine and said about 0.5M ammonium acetate are present in said reagent at a volume ratio of about 1:3, respectively.

57. In a process for preparing purified synthesized oligonucleotide, said process comprising treating a protected oligonucleotide with a composition comprising methylamine and eluting said treated synthesized oligonucleotide from a reverse phase purification cartridge, the improvement comprising adding to said treated synthesized oligonucleotide a composition comprising an additive selected from the group consisting of sodium chloride and ammonium acetate prior to eluting said treated synthesized oligonucleotide from the reverse phase purification cartridge.

58. In a process for synthesizing oligonucleotide, said process comprising treating a protected oligonucleotide with a composition comprising methylamine, the improvement comprising treating said protected oligonucleotide with a composition comprising methylamine and an additive selected from the group consisting of ammonium acetate and sodium chloride.

* * * * *